(12) United States Patent
Ottmar et al.

(10) Patent No.: US 6,630,679 B1
(45) Date of Patent: Oct. 7, 2003

(54) SAMPLE CHANGER FOR TRANSFERRING RADIOACTIVE SAMPLES BETWEEN A HOT CELL AND A MEASURING APPARATUS

(75) Inventors: Herbert Ottmar, Karlsruhe (DE); Georges Dockendorf, Eggenstein-Leopoldshafen (DE)

(73) Assignee: European Community (LU)

( * ) Notice: Subject to any disclaimer, the term of this patent is extended or adjusted under 35 U.S.C. 154(b) by 0 days.

(21) Appl. No.: 09/762,101
(22) PCT Filed: Jul. 28, 1999
(86) PCT No.: PCT/EP99/05419
§ 371 (c)(1), (2), (4) Date: Mar. 14, 2001
(87) PCT Pub. No.: WO00/08450
PCT Pub. Date: Feb. 17, 2000

(30) Foreign Application Priority Data

Aug. 5, 1998 (LU) .................................................. 90270

(51) Int. Cl.⁷ .............................. G01N 21/00; G01T 1/00
(52) U.S. Cl. .................................... 250/453.11; 250/328
(58) Field of Search ....................... 250/453.11, 454.11, 250/328

(56) References Cited

U.S. PATENT DOCUMENTS

| 3,654,472 A | 4/1972 | Hof et al. .................... 250/106 |
| 3,776,284 A | 12/1973 | Guyer et al. .................. 141/65 |
| 3,792,276 A | * 2/1974 | Toman et al. ................ 250/369 |
| 3,852,599 A | * 12/1974 | Smith .......................... 250/328 |
| 3,926,323 A | * 12/1975 | Frank et al. .............. 250/491.1 |
| 4,001,585 A | 1/1977 | Coutarel ...................... 250/328 |
| 4,220,855 A | * 9/1980 | Johnson ....................... 250/328 |
| 5,290,513 A | * 3/1994 | Berthold et al. ............. 250/328 |

OTHER PUBLICATIONS

Coquerelle M. et al., "Refurbishing of a Hot Cell for Non–Destructive Testing" Remote Systems Technology Proceedings, Nov. 1, 1991, pp. 101–106.

* cited by examiner

Primary Examiner—Bruce Anderson
(74) Attorney, Agent, or Firm—Smith, Gambrell & Russell, LLP

(57) ABSTRACT

A sample changer for transferring radioactive samples between a hot cell (12) and a measuring apparatus (10), as e.g. a hybrid K-edge densitometer, comprises a transfer channel (28) axially extending through a tubular containment (22) between the charging/discharging port and the measuring window section D. A recipient (24), with at least one compartment (100) for receiving therein a radioactive sample, is arranged in the transfer channel (28) so as to be movable therethrough. A threaded spindle (44) is rotatably housed in a spindle channel (42) below the transfer channel (28). A coupling (46) passing in a sealed manner through the closed rear end section connects a stepping motor (34) to the threaded spindle (44). A longitudinally guided support carriage supports the magazine (24) and engages the threaded spindle (44), so as to be subjected to a translational movement upon rotation of the spindle (44).

26 Claims, 7 Drawing Sheets

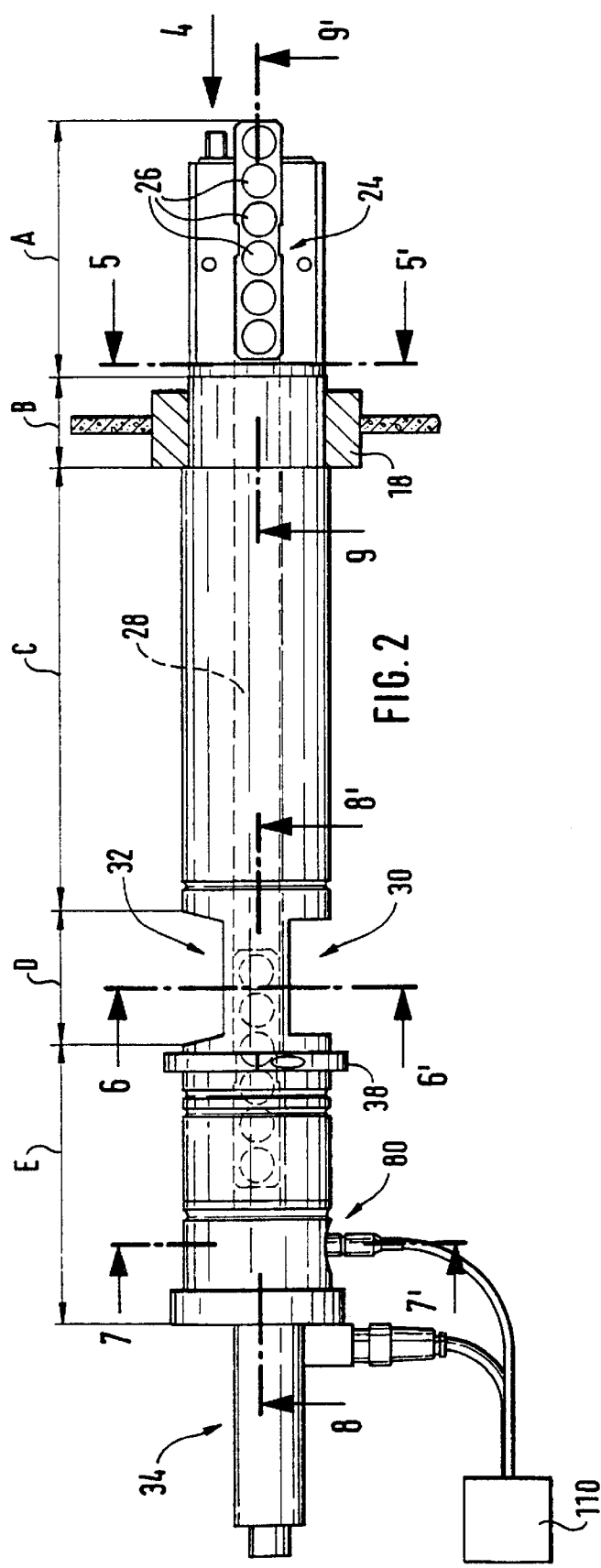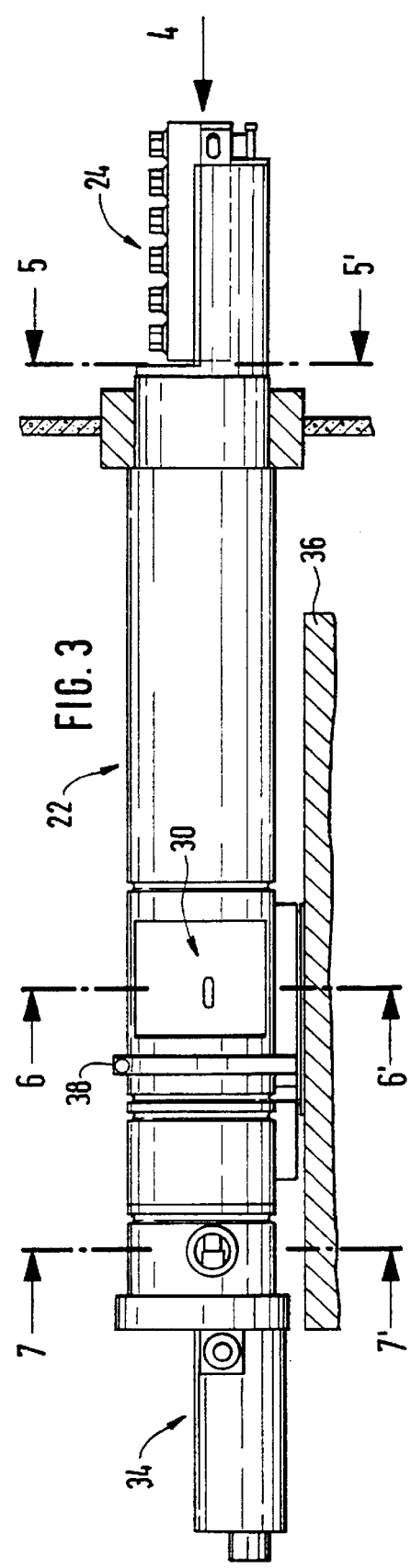

Figure 1:
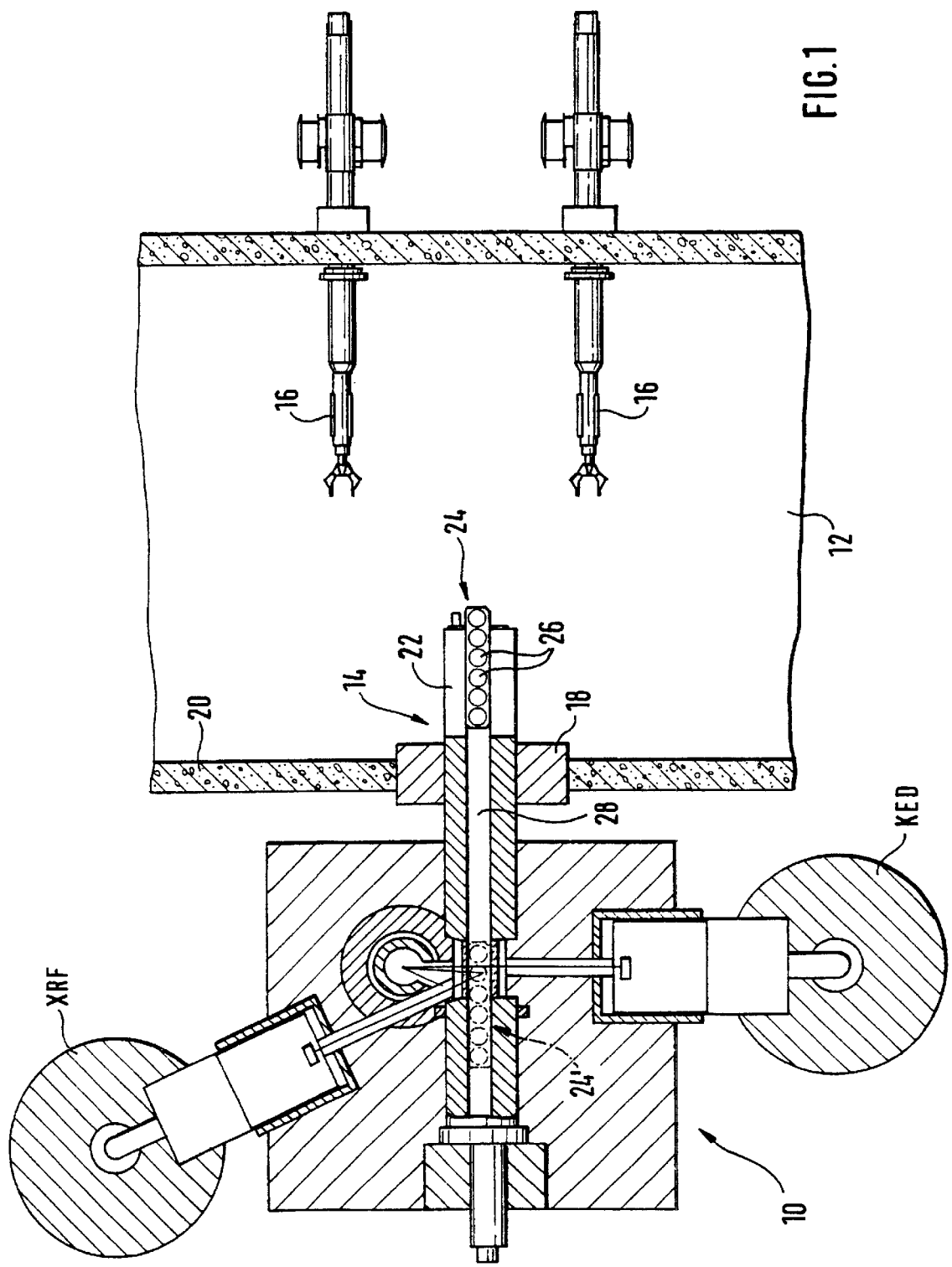

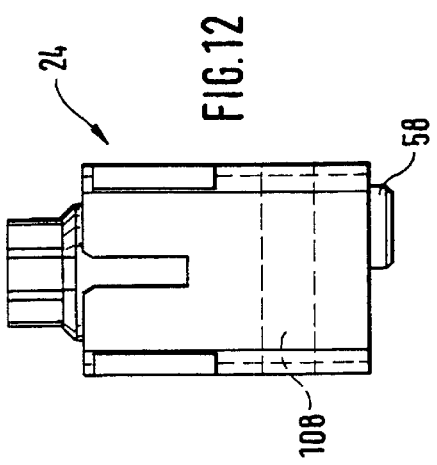
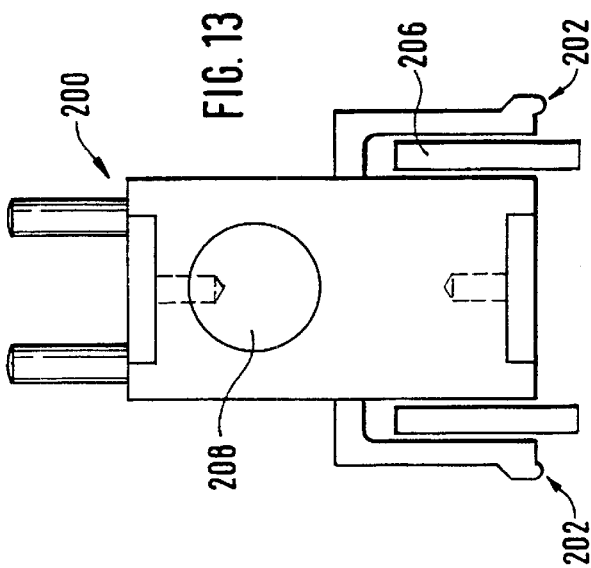
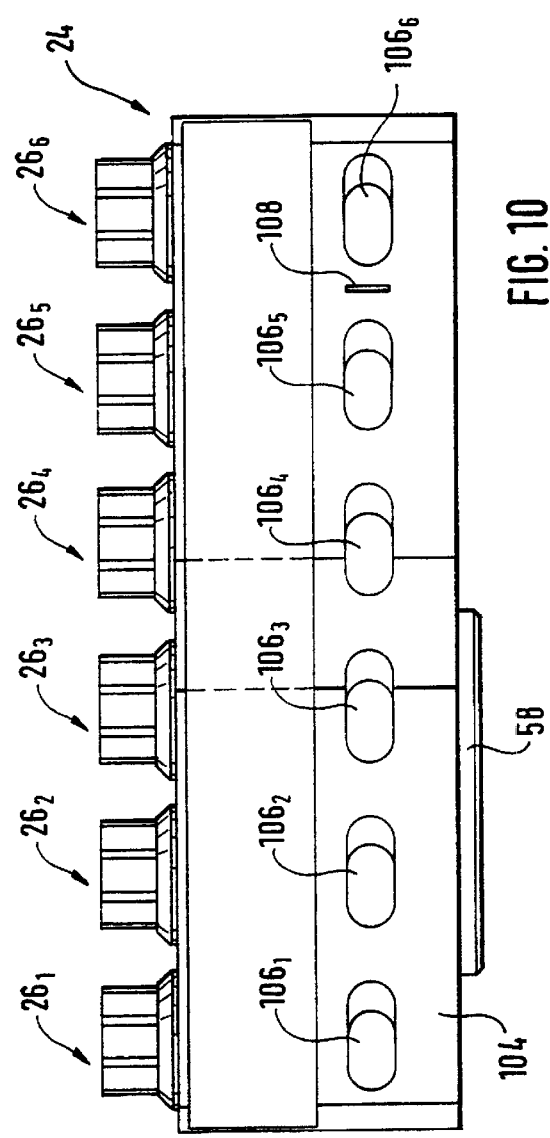
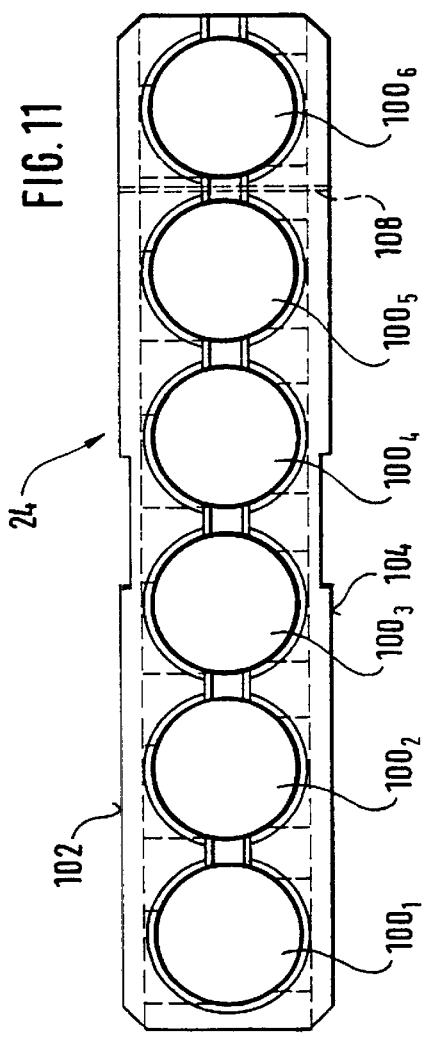

SAMPLE CHANGER FOR TRANSFERRING RADIOACTIVE SAMPLES BETWEEN A HOT CELL AND A MEASURING APPARATUS

INTRODUCTION

The present invention relates in general to a sample changer for transferring radioactive samples between a hot cell and a measuring apparatus. It relates in particular to such a sample changer for use with a hybrid K-edge densitometer. It also relates to a hybrid K-edge densitometer measuring facility.

A hybrid K-edge densitometer (HKED) measuring facility, which allows to determine uranium and plutonium concentrations in liquors, as obtained e.g. after dissolution of various types of nuclear materials (e.g. irradiated reactor fuel elements), is disclosed in the publication: "The Hybrid K-Edge/K-XRF Densitometer: Principles—Design—Performance", H. Ottmar, H. Eberle, Report KfK 4590, February 1991, Kernforschungszentrum Karlsruhe.

This prior art HKED measuring facility comprises a hot cell, for safely handling the samples to be measured with telemanipulators, the HKED measuring apparatus itself, which is located outside the hot cell, and a sample transfer tube, which is connecting the measuring apparatus to the hot cell. This sample transfer tube consists of a stainless steel tube with an outer diameter of 8 cm, which extends from the measuring apparatus through an existing adapter flange into the hot cell. It includes a charging/discharging port in the hot cell and a measuring window section traversed by the X-ray measuring beams in the measuring apparatus. A transfer channel extends axially through the stainless steel tube from the charging/discharging port into the measuring window section. It has a rectangular cross-section to accommodate a monobloc sledge, so that the latter is easily gliding through the transfer channel. This monobloc sledge has a single compartment for receiving therein a receptacle containing two vials with the sample to be measured. The rear end section of the stainless steel tube is closed and includes a micro-switch and magnet.

For carrying out a measurement in the prior art HKED facility, the receptacle with the sample is placed into the sledge when the latter is located in the charging/discharging port of the sample transfer tube. The sledge is then transferred through the transfer channel of the sample transfer tube from the charging/discharging port into the measuring window section. To carry out this transfer, the operator has to manipulate, with the telemanipulators of the hot cell, a rod of about 80 cm, in order to push the sledge through the transfer channel into its measuring position within the measuring window section. When the sledge is positioned in its measuring position, it actuates the micro-switch in the rear end section of the transfer tube, thus enabling the measurement procedure. The magnet in the rear end section of the transfer tube maintains the sledge in place during the measurement, thus assuring a reproducible positioning of the sample in the measuring beams. When the measurement is finished, the operator uses again the telemanipulators and the rod to pull the sledge back into the charging/discharging port, where the receptacle with the samples is lifted out of the sledge.

The sample transfer tube of the prior art HKED facility has following indisputable advantages:

- it provides a safe containment for the transfer of the samples between the hot cell and the measuring apparatus;
- it provides a high degree of operational reliability under the severe environment conditions in the hot cell, which are characterised e.g. by the presence of acid vapours and extreme levels of gamma radiation;
- it is very compact, so that it can be mounted in a standard flange adapter of a hot cell;
- it allows to position the focal spot of a shielded X-ray tube in the measuring window section at a very short distance from the center of the sample to be measured;
- it assures a very accurate reproducible positioning of the sample in the measurement position without relying on electric or electronic equipment located inside the containment.

A major disadvantage of the prior art sample transfer tube is that it requires manual intervention for changing the sample after a measurement.

OBJECT OF THE INVENTION

A technical problem underlying the present invention is to automate transfer and exchange of samples between the hot cell and the measuring apparatus located outside the hot cell, while generally maintaining the above mentioned advantages of the manually operated sample transfer tube. This problem is solved by a sample changer as claimed in claim 1.

GENERAL DEFINITION OF THE INVENTION

The sample changer of the present invention includes a tubular containment having a charging/discharging port, which is introduced into the hot cell; a transfer section, which extends into the measuring apparatus outside the hot cell; a measuring window section, which is traversed by a measuring beam inside the measuring apparatus; and an closed rear end section, which is located at the opposite end of the charging/discharging port. A recipient with at least one compartment for receiving therein a radioactive sample is arranged in a transfer channel extending axially through the tubular containment between the charging/discharging port and the measuring window section. When located in the charging/discharging port within the hot cell, this recipient can be charged and discharged by means of telemanipulators. In accordance with an important aspect of the present invention, a threaded spindle is rotatably housed in a spindle channel arranged in the tubular containment below the transfer channel. This threaded spindle extends between the charging/discharging port and the measuring window section. A stepping motor is located at the outside of the tubular containment and is connected to the threaded spindle via a coupling sealingly passing through the closed rear end section of the tubular containment. A longitudinally guided support carriage, which is supporting the recipient in the transfer channel, engages the threaded spindle so as to be subjected to a translational movement upon rotation of the spindle. It follows that the transfer of the samples from the hot cell into the measuring apparatus and vice versa, can be entirely automated and no longer needs remote handling operations with telemanipulators. The linear drive, which is used in the sample changer of the present invention for automating the transfer of the samples, has a high operational reliability and is capable of providing an excellent positioning accuracy of the samples in the measuring apparatus. It is integrated into the sample changer in such a way that the cross-section of the containment need not be increased with regard to a traditional sample transfer tube with manual sample transfer. Thus it will be possible to install the sample changer into an existing hot cell adapter flange, just as the prior art transfer tube. Last but not least, it will be appreciated in particular that the sample changer of the present invention is characterized by a strict separation of electrical and mechanical components of its drive. Only fail-safe mechanical components are kept within the alpha containment of the hot cell with its hostile ambient conditions (radiation, acid vapors . . . ,). Electrical components, as the stepping motor, are located outside the containment, so that they are easily accessible for maintenance and replacement.

In a preferred embodiment of the invention, the sample changer further includes a plug-in coupling device, for coupling one end of the threaded spindle to the coupling, and a bearing block for supporting the opposite end of the threaded spindle. This bearing block is slidably fitted in the spindle channel, and the spindle channel is axially accessible from the hot cell, so that the threaded spindle and its bearing block can be axially withdrawn from the spindle channel into the hot cell. It follows that—for maintenance and or replacement—the contaminated mechanical components of the linear drive may be safely withdrawn with the help of telemanipulators into the hot cell.

To be capable of easily dismounting the support carriage by means of telemanipulators, without removing the spindle, the carriage preferably includes threaded engaging means that are engaging exclusively the upper half of the threaded spindle. It follows that the carriage may be simply lifted from the threaded spindle by means of the telemanipulators.

In a preferred embodiment, the support carriage includes two support blocks, wherein each of these support blocks comprises a cylindrically curved threaded surface engaging exclusively the upper half of the threaded spindle. This block rests advantageously by means of downwardly oriented runners on two lateral support surfaces in the spindle channel and is laterally guided in the spindle channel.

The support carriage and the recipient could of course be fixed together so as to form one single element. However, in order to facilitate maintenance and to allow the use of different types of recipients, it is suggested to conceive the recipient and the carriage as two independent elements, wherein interlocking means on the recipient and the support carriage are co-operating for reproducibly positioning the recipient on the support carriage. Thus the recipient can be removed from the support carriage, without affecting the positioning accuracy. In a preferred embodiment, the support carriage includes for example a support plate connecting the support blocks together and providing a support surface for the recipient, wherein the recipient and the support plate include interlocking means co-operating for reproducibly positioning the recipient on the support plate.

In a preferred embodiment of the invention, the recipient is a magazine including several compartments arranged in axial alignment within the magazine. Control means control the stepping motor so as to adjust each of the different compartments of the magazine subsequently in the measuring beam. It will be appreciated that such a sample changer allows fully automated measurements on several measurement samples.

For reproducibly positioning the different compartments of the sample magazine into the measuring beam, the control means include advantageously a slit aperture in the magazine and computer means which are operatively coupled to means for measuring the intensity of the measuring beam passing through the slit aperture and to the stepping motor. The slit aperture is driven through the measuring beam and the computer means compute a final reference position of the stepping motor corresponding to the position of the stepping motor in which the intensity of the measuring beam passing through the slit aperture is maximum. This final reference position is then used for computing the number of steps to be executed by the stepping motor in order to position each of the compartments of the magazine accurately in the measuring beam.

In order to facilitate the positioning operation with the slit aperture, the sample changer further includes a position detector to be triggered by the support carriage, when the latter is in a predetermined position in the measuring window section. Computer means, which are operatively coupled to the position detector and to the stepping motor, compute an initial reference position of the stepping motor corresponding to the position of the stepping motor in which the position detector is triggered by the support carriage. This initial reference position is then used for calculating the number of steps to be executed by the stepping motor in order to position the slit aperture at a predetermined distance from the measuring beam. The position detector is preferably an inductive position detector housed in a leakproof protection sheath within the rear end section of the containment and detecting the presence of a metallic flag fixed to the transfer carriage.

It will be appreciated that the present invention also provides a Hybrid K-Edge Densitometer (HKED) measuring facility for automated measurements on highly radioactive materials.

IDENTIFICATION OF THE DRAWINGS

Figure 4:
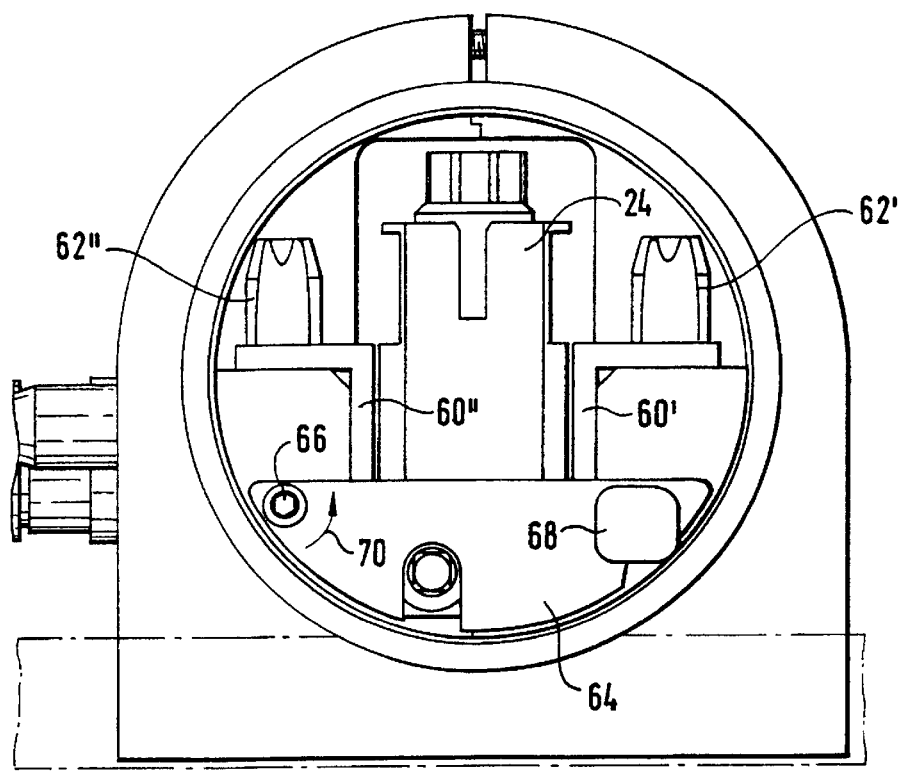
Figure 5:
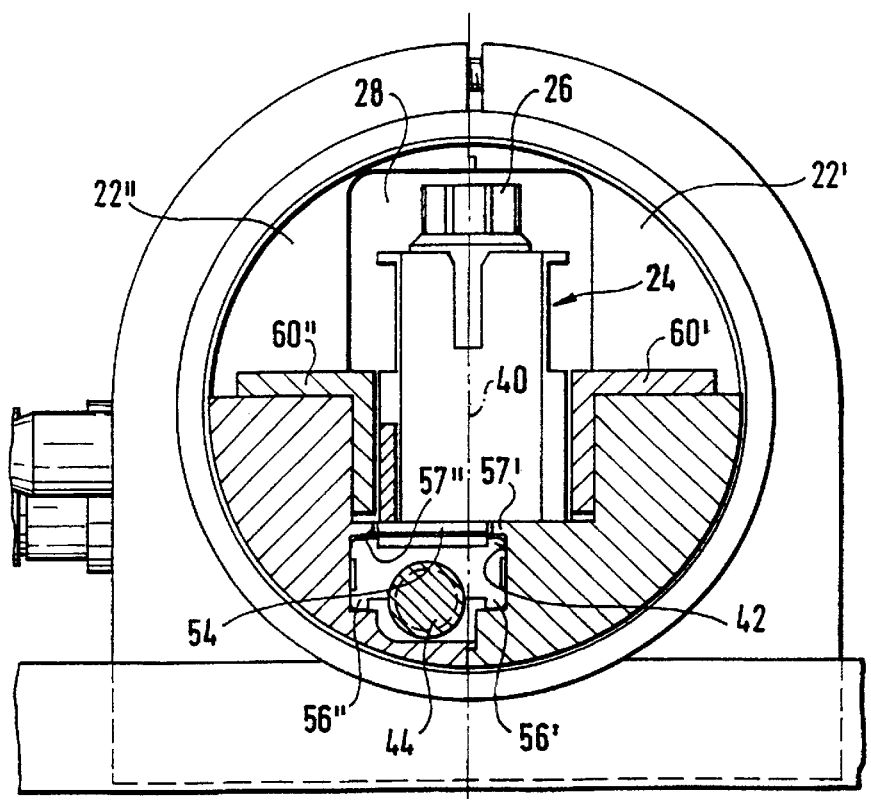
Figure 6:
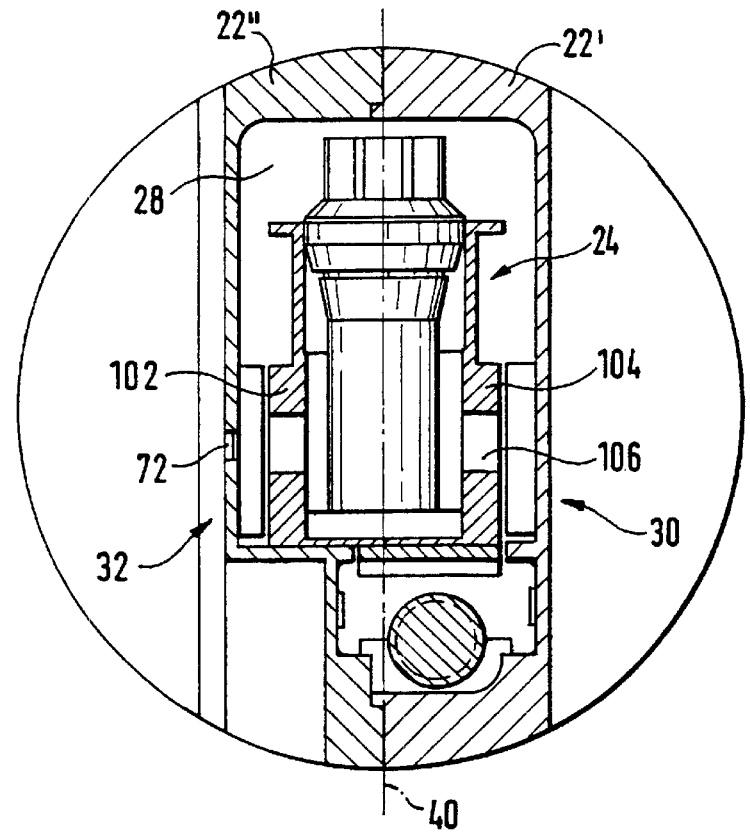
Figure 7:
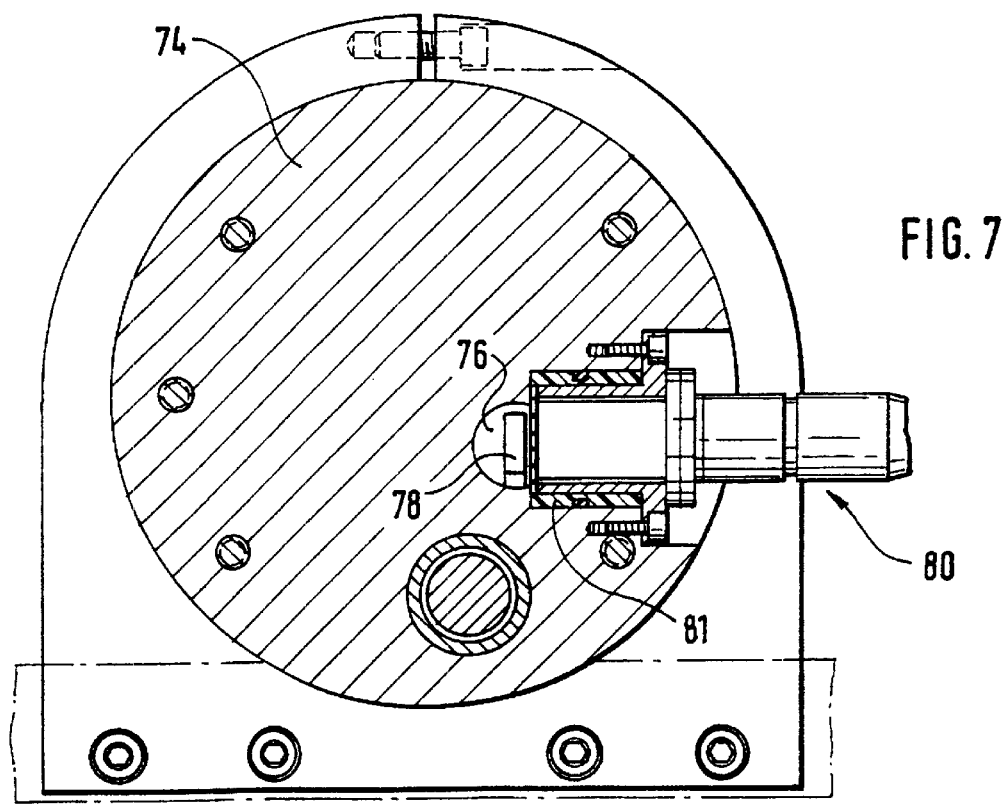
Figure 8:
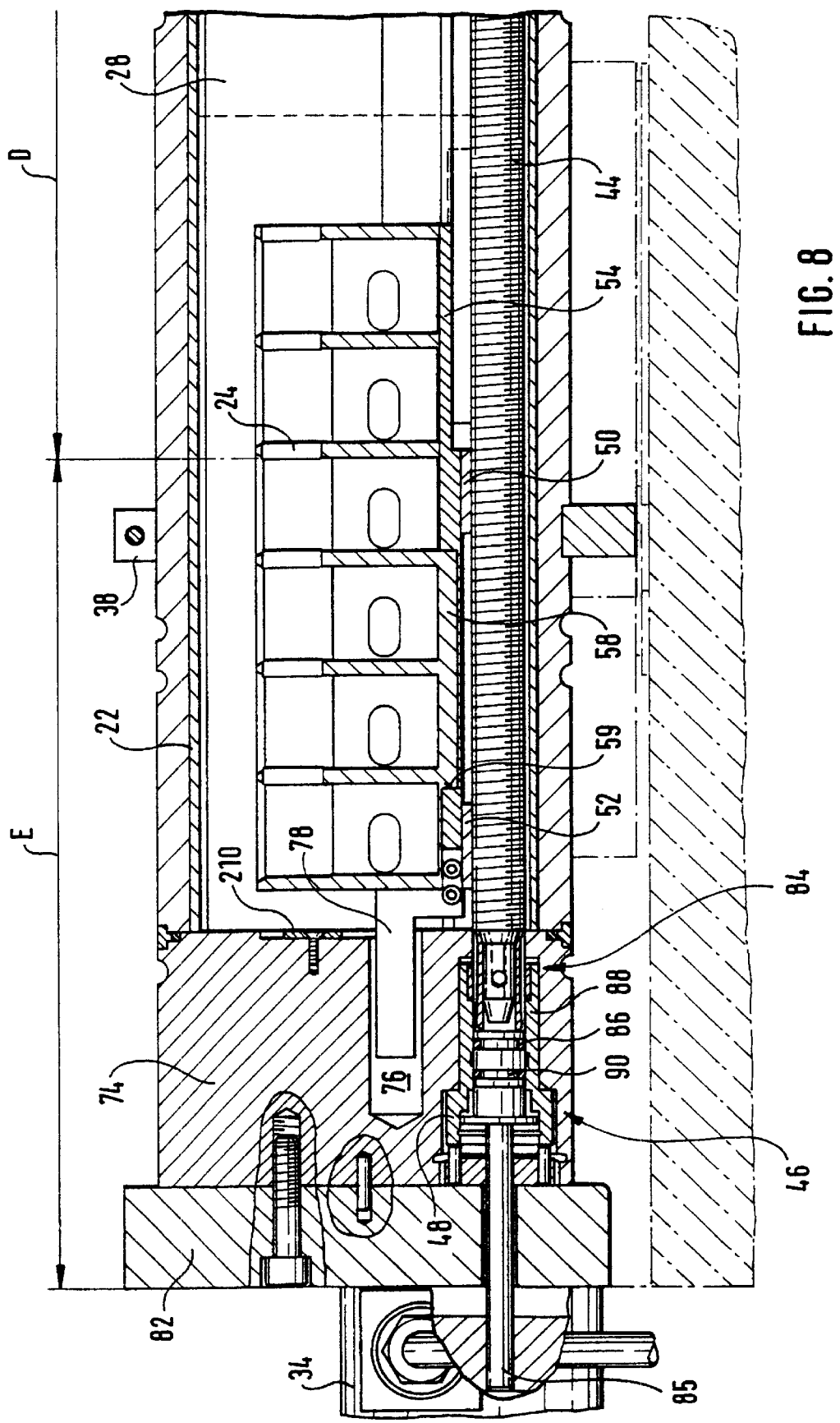
Figure 9:
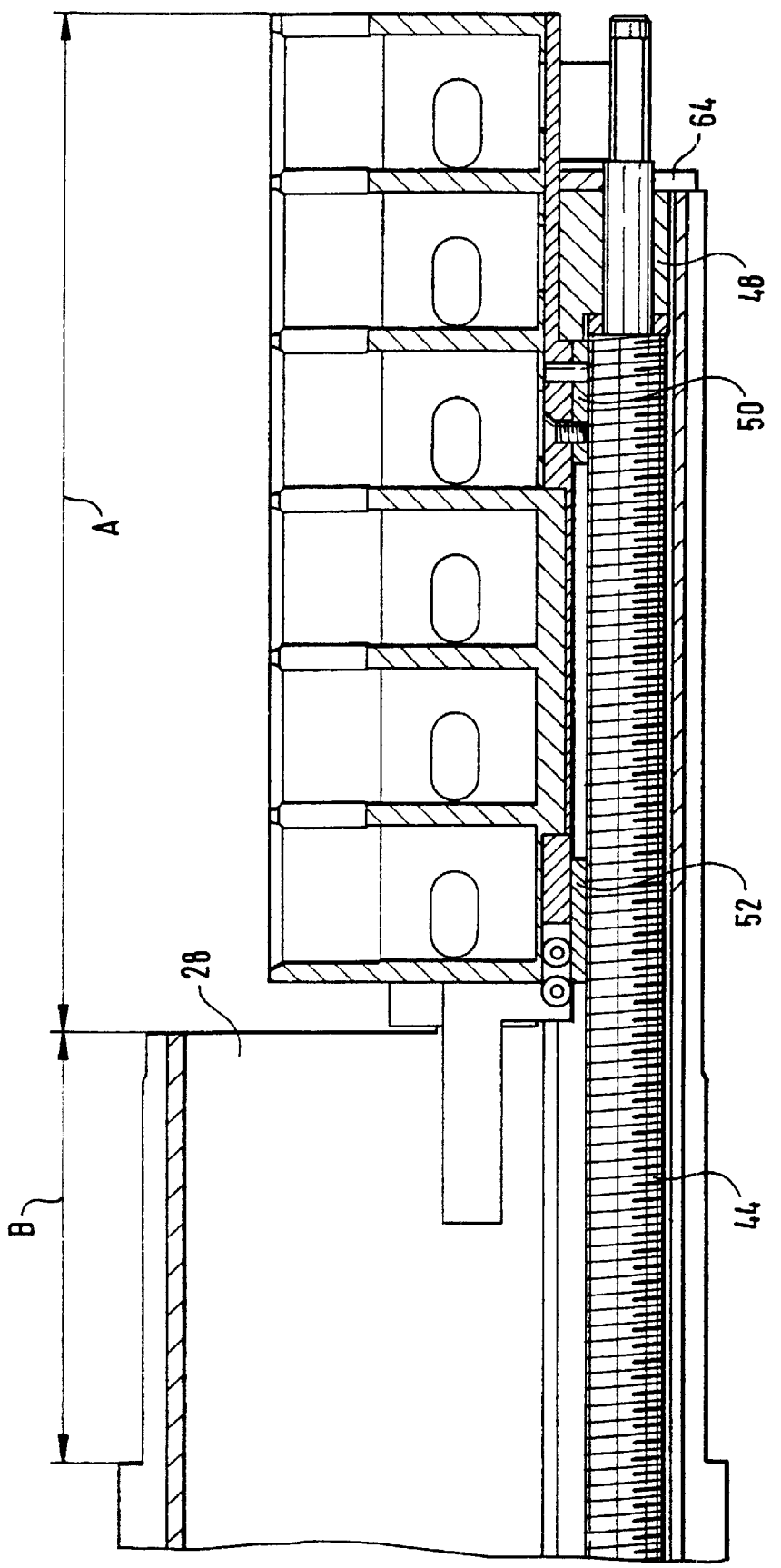

The present invention will now be described, by way of example, with reference to the accompanying drawings, in which:

FIG. 1: is a schematic cross-section through a Hybrid K-Edge Densitometer (HKED) measuring facility with a sample changer in accordance with the present invention;

FIG. 2: is a top view of the sample changer;

FIG. 3: is a side view of the sample changer;

FIG. 4: is an end view of the sample changer in the direction of arrow 4 in FIGS. 2 and 3;

FIG. 5: is a cross-sectional view of the sample changer, wherein the section is identified by arrows 5, 5' in FIGS. 2 and 3;

FIG. 6: is a cross-sectional view of the sample changer, wherein the section is identified by arrows 6, 6' in FIGS. 2 and 3;

FIG. 7: is a cross-sectional view of the sample changer, wherein the section is identified by arrows 7, 7' in FIGS. 2 and 3;

FIG. 8: is a detail view showing a longitudinal section through the sample changer as identified by arrows 8, 8' in FIGS. 2 and 3;

FIG. 9: is a detail view showing a longitudinal section through the sample changer as identified by arrows 9, 9' in FIGS. 2 and 3;

FIG. 10: is an elevation view of a sample magazine for the sample changer;

FIG. 11: is a top view of the sample magazine of FIG. 10; and

FIG. 12: is an end view of the sample magazine of FIG. 10;

FIG. 13: is an end view of a sledge conceived for using the sample changer as a manual transfer tube.

DETAILED DESCRIPTION OF THE PREFERRED EMBODIMENT OF THE INVENTION

FIG. 1 schematically shows a measuring facility comprising a shielded measuring apparatus 10, which is connected to a shielded hot cell 12 by means of a sample changer 14 in accordance with the present invention.

The exemplary measuring apparatus shown in FIG. 1 is a Hybrid K-Edge Densitometer (HKED), i.e. a special X-ray spectrometer designed for the analysis of uranium and plutonium concentrations in liquors, which are obtained after dissolution of various types of nuclear materials (e.g. irradiated reactor fuel elements). For more details with regard to the apparatus and to the measurement techniques it is referred to the document:—"The Hybrid K-Edge/K-XRF Densitometer: Principles—Design—Performance", Report KfK 4590, Kernforschungszentrum Karlsruhe (1991).

The hot cell 12 is a well shielded enclosure, in which highly radioactive materials can be manipulated safely by means of telemanipulators 16. The hot cell environment is characterised by the presence of highly corrosive acid vapours and extreme levels of gamma radiation. A standard adapter flange 18 is located in a wall 20 of the hot cell 12, opposite of the telemanipulators 16. A front-end of a tubular containment 22 penetrates through the standard adapter flange 18 into the hot cell 12. The greater part of the tubular containment 22 protrudes however out of the hot cell 12, where it provides a safe and leakproof containment penetrating into a cavity in the shielded measuring apparatus 10 located outside of the hot cell 12.

Still referring to FIG. 1, reference 24 points to a magazine located in a charging/discharging port at the front-end of the sample changer in the hot cell 12. This magazine 24 contains six receptacles 26 for measurement samples, which have been put into the magazine located in the charging/discharging port by means of the telemanipulators 16. The sample changer 14 automatically transfers the magazine 24, through a channel 28 in the tubular containment 22, into a measuring position within the measuring apparatus 10. It will be noted that the magazine is shown with dotted lines in the measuring position and identified with reference number 24'. The sample changer 14 then accurately positions each of the sample receptacles 26 in a highly collimated X-ray beam, so that the HKED can successively measure each of the samples. When all the samples contained in the magazine have been measured, the sample changer 14 automatically transfers the magazine 24 back into the charging/discharging position, where the receptacles 26 can be easily lifted out of the magazine 24 by means of the telemanipulators 16.

The structure of the sample changer 14 will now be described in detail with reference to drawings 2 to 9.

FIGS. 2 and 3 show more detailed views of the sample changer 14. It will be noted that the tubular containment may be divided into five sections (see FIG. 2):

a) a charging/discharging port A, located inside the hot cell 12, so that the receptacles 26 are within easy reach of the telemanipulators 16, when the receptacle magazine 24 is in a charging/discharging position within this charging/discharging port A;

b) a sealing section B, which is received in the standard adapter flange 18 of the hot cell 12, wherein the adapter flange 18 provides a sealed connection which is leakproof against alpha-particles;

c) a transfer section C, which extends from the adapter flange 18 into the measuring apparatus 10 and provides a containment and shielding function;

d) a measuring window section D, which provides a measuring window 30, 32 on each side of the channel 28, to which a X-ray generator, a X-ray fluorescence analyser (XRF) and a K-edge densitometer (KED) may e.g. be connected as shown in FIG. 1;

e) a rear end section E, to which a stepping motor 34 is fixed and which is itself supported on a mounting plate 36 by means of a clamp 38 (see FIG. 3).

FIGS. 5 to 7 show cross-sections through sections A, D and E of tubular containment 22 of the sample changer 14. It will first be noted that this tubular containment 22 is built up of two high-grade stainless steel shells 22', 22" connected together by electron beam welding in the region of the vertical plane passing through the centre line of the tubular containment 22. A half of the transfer channel 28 is milled in each of the two shells 22', 22" prior to their assembly. The cross-section of the channel 28 is only slightly bigger than the cross-section of carriage.24 having the receptacles 26 placed therein.

According to an important aspect of the present invention, a second channel 42 extends below the transfer channel 28 over the whole length of the latter. This channel 28 houses a spindle drive for moving the magazine 24 between its charging/discharging position and its measuring position and for adjusting the receptacles in the measuring position and is therefore referred to hereinafter "spindle channel 28".

The spindle drive will now be described in greater detail, referring simultaneously to FIGS. 5, 8 and 9. It includes a threaded spindle 44, which is connected to an output shaft of the stepping motor 34 by means of a special coupling 46 (see FIG. 8), and longitudinally extends through the entire spindle channel 28 into the charging/discharging port A, wherein its second end is supported in a bearing block 48 (see FIG. 8). A transfer carriage for the magazine 24 comprises two support blocks 50, 52, and a support plate 54, which is connecting the two support blocks 50, 52 together and provides a support surface for the magazine 24 in the transfer channel 28. As best seen on FIG. 5, each of the support blocks 50, 52 has a cylindrically curved surface comprising a thread portion engaging exclusively the upper half of the threaded spindle 44. The support blocks 50, 52 are laterally guided in the spindle channel 42 and rest on two lateral support surfaces in the spindle channel 42 by means of downwardly oriented runners 56', 56". Ribs 57', 57" project laterally into the spindle channel 42 so as to provide vertical limit stops for the threaded support blocks 50, 52 in the spindle channel 42. It will be noted that the support blocks 50, 52 and the support plate 54 are preferably made of polyethylene.

As shown more particularly on FIGS. 8 and 9, the magazine 24 rests on the support plate 54. A foot 58 projecting downwardly from the bottom of the magazine 24 (see also FIGS. 10 and 12) is received in a corresponding aperture 59 in the support plate 54, so that the magazine 24 is interlocked in a reproducible position on the support plate 54.

Referring simultaneously to FIGS. 4, 5 and 9, the charging/discharging port A, will now be described in greater detail. In this section A the tubular containment 22 is reduced to a kind of balcony that projects into the hot cell 12 and forms therein the charging/discharging port of the sample changer 14. In the balcony, the channel 28 has an open cross-section; i.e. only the lower half of the magazine 24 is received in the channel 28. The upper half of the magazine 24 and the receptacles 26 contained herein are freely accessible to the telemanipulators 16. Two guiding profiles 60', 60" provide lateral guidance for adjusting the magazine 24 on the support plate 54 of the transfer carriage, in case the magazine 24 must be exchanged. These guiding profiles 60', 60" are preferably conceived as wearing parts, made for example of polyethylene. They can be easily dismounted with the telemanipulators 16 by unscrewing securing screws 62', 62". In FIG. 4, reference number 64 points to a flap that is axially closing the spindle channel 42, so as to provide an axial limit stop for the bearing block 48 in the spindle channel 42. When a securing screw 68 is loosened, this flap 64 can be pivoted about an axis 66 in the direction of arrow 70, so as to provide an unlimited axial access to the spindle channel 42. It follows that the telemanipulators 16 can axially withdraw the spindle 44, the bearing block 48 and the transfer carriage out of the spindle channel 42 into the hot cell 12. A new spindle 44 and a new bearing block 48 can be easily mounted in the same manner. For mounting a new carriage, it may however be easier to first dismount the profiles 62', 62" and then to introduce the carriage from above through the transfer channel 28 and adequate cut-outs in the ribs 57', 57" into the spindle channel 42.

Sections B and C of the tubular containment 22 both have a cylindrical shape. These two sections provide a shielded and leakproof transfer containment for the magazine 24. As shown in FIG. 6, the cylindrical shape of the tubular containment 22 is considerably flattened in the measuring window section D, so as to allow the measuring apparatuses to be placed closest to the magazine 24 containing the samples to be measured. The measuring windows 30 and 32 are two flat, thin walls arranged symmetrically to the centre plane of the magazine 24 in the measuring position. Measuring window 32 includes a groove 72, which is locally reducing the wall thickness of measuring window 32 for the passage of the measuring beam.

As shown on FIG. 8, channel 28 extends into the end section E where it is hermetically closed by means of a closing plate 74. The latter houses the special coupling 46 for the threaded spindle and a cavity 76 for receiving a metallic flag 78 attached to the support plate 54 of the carriage. As shown on FIG. 7, a cross-hole extends into the cavity 76. This cross-hole houses a leakproof protection sheath 81 in which a position detector 80, preferably an inductive position detector, is mounted. This position detector 80 is used for detecting the position of flag 78 in cavity 76 and thereby the position of the transfer carriage supporting the magazine 24. It acts as a limit switch to stop the transfer carriage and to define a reference position for the stepping motor. A shielding plate 82, having a cross-section slightly larger than the closing plate 74, separates the stepping motor 34 from the radioactive protection containment formed by the tubular containment 22.

Referring again to FIG. 8, it will be noted that the special coupling 46 housed in the closing plate 74 comprises on one end a plug-in type connection system 84 for the free end of the threaded spindle 44, and on the other end a connection shaft 85 for the stepping motor 34. This connection shaft 85 extends through a passage in the shielding plate 82. A shaft seal, comprising e.g. two sealing rings 86, is arranged between a stationary shell 88, which is housed itself in sealed manner in a chamber of the closing plate 74, and a revolving shaft 90 of the coupling 46. This double shaft seal 86 avoids a leakage of radioactive and corrosive gases along the connection shaft 85 to the outside and into the interior of the stepping motor 34. A strict separation of electrical and mechanical components is achieved in this manner, keeping the electrical components outside the containment for easy access and replacement and protecting it against radioactive contamination and highly corrosive gases.

FIGS. 10, 11 and 12 show more detailed views of the magazine 24 used with the sample changer 14. The displayed magazine 24 defines six compartments 100$_i$ arranged in axial alignment within the magazine, each of the compartments 100$_i$ being designed for receiving therein a sample receptacle 26$_i$, so that the receptacle 26$_i$ is reproducibly and accurately positioned within the magazine 24. It will of course be possible to work with magazines having either more than six compartments or less than six compartments. The magazine 24, which may be made for example of titanium, has two side-walls 102 and 104 laterally delimiting the compartments 100$_i$. Each of the two side-walls 102 and 104 includes for each of the compartments 100$_i$ a measuring opening 106$_i$, wherein the two measuring openings of one compartment 100$_i$ are arranged opposite each other, so as to define a path for the measuring beam through the receptacle 26$_i$ placed in the respective compartment 100$_i$.

Reference number 108 points to a slit aperture incorporated in the magazine 24. This slit aperture 108, which has a very small width (e.g. a width of 0.2 mm) is used for a high accuracy positioning (e.g. better than 0.05 mm) of the magazine 24 by measuring and evaluating the intensity profile of a beam through the slit aperture.

The normal operation of sample changer 14 is as follows. The operator uses telemanipulators 16 to put the receptacles 26 containing the radioactive samples to be analysed into the compartments 100$_i$ of the magazine 24, which is positioned in the charging/discharging port A. When the charging of the magazine 24 is finished, an automatic measuring process is started by a measuring computer 110 (see FIG. 2). This measuring process has following steps:

a) driving the transfer carriage with the magazine 24 in the direction of section E with the spindle drive;

b) detecting the flag 78 of the transfer carriage with the position detector 80, so as to stop the transfer carriage in a predetermined position in section E;

c) using said predetermined position of the transfer carriage in section E as a reference position for a step counter;

d) executing a predetermined number of steps with the stepping motor 34, so as to bring the slit aperture 108 in the magazine 24 at a small, predetermined distance from the highly collimated measuring beam. In the pilot apparatus, the slit aperture 108 is e.g. brought at a distance of 1 mm from the highly collimated X-ray beam;

e) executing a predetermined number of steps with the stepping motor 34, so as to drive the slit aperture 108 through the measuring beam. In the pilot apparatus, the stepping motor 34 executes e.g. 20 steps, each step providing an increment of 0.1 mm. The distance over which the slit aperture 108 is moved is consequently ten times greater than the width of the slit aperture 108;

f) measuring for each step the intensity of the measuring beam passing through the slit aperture 108. In the pilot apparatus, the K-Edge Detector measures e.g. the intensity of the highly focussed X-ray beam passing through the slit aperture 108;

g) calculating the beam intensity maximum (i.e. the position in which the slit aperture is best adjusted within the measuring beam) in function of the number of steps executed by the stepping motor (using e.g. the least-squares-fit method) and taking this position of the stepping motor 34 as a new reference position;

h) calculating, on the basis of the new reference position, the steps to be executed by the stepping motor 34 in order to position each of the compartments 100$_i$ of the magazine 24 accurately in the measuring beam, wherein the distance between the slit aperture 108 and the centre line of each compartment is known with great accuracy (dimensional tolerance 0.01 mm or better);

i) successively executing the calculated number of steps with the stepping motor 34 for adjusting each of the compartments 100$_i$ of the magazine 24 in the measuring beam and executing the measurement on the sample contained in the respective compartment 100$_i$;

j) driving the transfer carriage with the magazine 24 back into section A, when all the samples have been measured.

It will be appreciated that in case of a failure of the linear drive mechanism, the sample changer of the present invention can be used, without any mechanical modifications, as a sample transfer tube for manual exchange of the measurement samples. In this case the magazine 24 is removed from the carriage and a special sledge 200 (see FIG. 13) is introduced into the transfer channel 28 in the charging/discharging port A. Lateral runners 202, 204 support the sledge 200 on sliding surfaces located in the transfer channel 28 on each side of the spindle channel 42. It will be noted that the sledge 200 is conceived to glide over the support carriage, wherein the flag 78 of the support carriage passes through a lateral channel 206 in the sledge. The support carriage may consequently remain in the sample changer even when the latter is used as manual sample transfer tube. The sledge includes in its rear end a cavity for receiving a recipient with the measurement sample. A handling rod, which is slightly longer than the transfer channel 28, is connected in an articulated manner to the rear end of the sledge, so that the latter can be pushed with the help of the telemanipulators 16 into the measuring window section. The front end of the sledge supports a magnet 208 which co-operates with a soft iron plate 210 in the end section E of the tubular containment 22 (see FIG. 8) to maintain the sledge in place during the measurement. The distance between the magnet 208 in the front end of the sledge and the central axis of the recipient with the measurement sample in the rear end of the sledge can be changed by means of an adjusting screw, which is capable of axially moving the magnet on the sledge. Thus it becomes possible to preset the measuring position of the sample recipient within the measuring window section of the tubular containment 22 with great precision. When the measurement of the sample is finished, the sledge is pulled back into the charging/discharging port A with the help of the rod and the telemanipulators 16.

What is claimed is:

1. A sample changer for transferring radioactive samples between a hot cell and a measuring apparatus located outside said hot cell, said sample changer comprising:
   a tubular containment having a charging/discharging port to be introduced into said hot cell, a transfer section, which extends into said measuring apparatus outside said hot cell, a measuring window section to be traversed by a measuring beam inside said measuring apparatus, and an closed rear end section located at said opposite end of said charging/discharging port;
   a recipient with at least one compartment for receiving therein a radioactive sample, said recipient being arranged in a transfer channel extending axially through said tubular containment between said charging/discharging port and said measuring window section;
   a threaded spindle rotatably housed in a spindle channel arranged in said tubular containment below said transfer channel, said threaded spindle extending between said charging/discharging port and said measuring window section;
   a stepping motor located at the outside of said tubular containment;
   a coupling connecting said stepping motor to said threaded spindle, said coupling passing sealingly through said closed rear end section; and
   a longitudinally guided support carriage, which is supporting said recipient in said transfer channel, said support carriage engaging said threaded spindle so as to be subjected to a translational movement upon rotation of said spindle.

2. The sample changer as claimed in claim 1, further including:
   a plug-in coupling device for coupling one end of said threaded spindle to said coupling; and
   a bearing block for supporting the opposite end of said threaded spindle, said bearing block being slidably fitted in said spindle channel;
   wherein said spindle channel is axially accessible from said hot cell, so that said threaded spindle and its bearing block can be axially withdrawn from said spindle channel into said hot cell.

3. The sample changer as claimed in claim 1, wherein said support carriage includes threaded engaging means engaging exclusively said upper half of said threaded spindle.

4. The sample changer as claimed in claim 3, wherein said support carriage includes two support blocks, each support block having:
   a cylindrically curved surface comprising a thread portion engaging exclusively said upper half of said threaded spindle; and
   downwardly oriented runners resting on two lateral support surfaces in said spindle.

5. The sample changer as claimed in claim 4, wherein each support block is laterally guided in said spindle channel.

6. The sample changer as claimed in claim 4, wherein:
   said support carriage further includes a support plate connecting said support blocks together and providing a support surface for said recipient; and
   said recipient and said support plate further include interlocking means co-operating for reproducibly positioning said recipient on said support plate.

7. The sample changer as claimed in claim 1, comprising interlocking means on said recipient and said support carriage, said interlocking means co-operating for reproducibly positioning said recipient on said support carriage.

8. The sample changer as claimed in claim 1, wherein:
   said recipient is a magazine including several compartments arranged in axial alignment within said magazine; and
   a control means is associated with said stepping motor, said control means being capable of controlling said stepping motor so as to position each of said different compartments of said magazine subsequently in said measuring beam.

9. The sample changer as claimed in claim 8, wherein said control means include:
   a slit aperture in said magazine;
   measuring means for measuring the intensity of said measuring beam passing through said slit aperture;
   a computer mews operatively coupled to said measuring means and to said stepping motor; said computer means being capable of computing a final reference position of said stepping motor corresponding to said position of said stepping motor in which the intensity of said measuring beam passing through said slit aperture is maximum, and of computing on the basis of said reference position the number of steps to be executed by said stepping motor in order to position each of said compartments accurately in said measuring beam.

10. The sample changer as claimed in claim 9, wherein said control means further includes:
   a position detector located outside of said tubular containment, said position detector being triggered by said support carriage, when the latter is in a predetermined position in said measuring window section;
   computer means operatively coupled to said position detector and to said stepping motor for computing a initial reference position of said stepping motor corresponding to the position of said stepping motor in which said position detector is triggered by said support carriage and for calculating the number of steps to be executed by said stepping motor in order to position said slit aperture at a predetermined distance from said measuring beam.

11. The sample changer as claimed in claim 10, wherein said position detector is an inductive position detector housed in a leakproof protection sheath within said rear end section of said containment, said transfer carriage including a metallic flag co-operating with said inductive position detector.

12. The sample changer as claimed in claim 1, wherein said tubular containment has a sealing section to be sealingly received in a standard adapter flange of said hot cell.

13. The sample changer as claimed in claim 1, wherein said tubular containment has a cylindrical shape in said transfer section which is considerably flattened in said measuring window section.

14. A hybrid K-edge densitometer measuring facility including a hot cell with an adapter flange;
   a hybrid K-edge densitometer located outside said hot cell; and
   a sample changer for transferring radioactive samples between said hot cell and said hybrid K-edge densitometer; said sample changer comprising:
   a tubular containment having a charging/discharging port to be introduced into said hot cell, a transfer section, which extends into said hybrid K-edge densitometer, a measuring window section to be traversed by a measuring beam inside said hybrid K-edge densitometer, and an closed rear end section located at said opposite end of said charging/discharging port;
   a recipient with at least one compartment for receiving therein a radioactive sample, said recipient being arranged in a transfer channel extending axially through said tubular containment between said charging/discharging port and said measuring window section;
   a threaded spindle rotatably housed in a spindle channel ranged in said tubular containment below said transfer channel, said threaded spindle extending between said charging/discharging port and said measuring window section;
   a stepping motor located at the outside of said tubular containment; a coupling connecting said stepping motor to said threaded spindle, said coupling passing sealingly throb said closed rear end section; and
   a longitudinally guided support carriage, which is supporting said recipient in said transfer channel, said support carriage engaging said threaded spindle so as to be subjected to a translational movement upon rotation of said spindle.

15. The hybrid K-edge densitometer as claimed in claim 14, further including:
   a plug-in coupling device for coupling one end of said threaded spindle to said coupling; and
   a bearing block for supporting the opposite end of said threaded spindle, said bearing block being slidably fined in said spindle channel;
   wherein said spindle channel is axially accessible from said hot cell, so that said threaded spindle and its bearing block can he axially withdrawn from said spindle channel into said hot cell.

16. The hybrid K-edge densitometer as claimed in claim 14, wherein said support carriage includes threaded engaging means engaging exclusively said upper half of said threaded spindle.

17. The hybrid K-edge densitometer as claimed in claim 16, wherein said support carriage includes two support blocks, each support block having:
   a cylindrically curved surface comprising a thread portion engaging exclusively said upper half of said threaded spindle; and
   downwardly oriented runners resting on two lateral support surfaces in said spindle channel.

18. The hybrid K-edge densitometer as claimed in claim 17, wherein each support block is laterally guided in said spindle channel.

19. The hybrid K-edge densitometer as claimed in claim 18, wherein:
   said support carriage further includes a support plate connecting said support blocks together and providing a support surface for said recipient; and
   said recipient and said support plate further include interlocking means co-operating for reproducibly positioning said recipient on said support plate.

20. The hybrid K-edge densitometer as claimed in claim 14, comprising interlocking means on said recipient and said support carriage, said interlocking means co-operating for reproducibly positioning said recipient on said support carriage.

21. The hybrid K-edge densitometer as claimed in claim 14, wherein said recipient is a magazine including several compartments ranged in axial alignment within said magazine; and
   a control means is associated with said stepping motor, said control means being capable of controlling said stepping motor so as to position each of said different compartments of said magazine subsequently in said measuring beam.

22. The hybrid K-edge densitometer as claimed in claim 21, wherein said control means include:
   a slit aperture in said magazine;
   measuring means for measuring the intensity of said measuring bean passing through said slit aperture;
   a computer means operatively coupled to said measuring means and to said stepping motor; said computer means being capable of computing a final reference position of said stepping motor corresponding to said position of said stepping motor in which the intensity of said measuring beam passing through said slit aperture is maximum, and of computing on the basis of said reference position the number of steps to be executed by said stepping motor in order to position each of said compartments accurately in said measuring beam.

23. The hybrid K-edge densitometer as claimed in claim 22, wherein said control means further includes:

a position detector located outside of said tubular containment, said position detector being triggered by said support carriage, when the taller is in a predetermined position in said measuring window section;

computer means operatively coupled to said position detector and to said stepping motor for computing a initial reference position of said stepping motor corresponding to the position of said stepping motor in which said position detector is triggered by said support carriage and for calculating the number of steps to be executed by said stepping motor in order to position said slit aperture at a predetermined distance from said measuring beam.

24. The hybrid K-edge densitometer as claimed in claim 23, wherein said position detector is an inductive position detector housed in a leakproof protection sheath within said rear end section of said containment, said transfer carriage including a metallic flag co-operating with said inductive position detector.

25. The hybrid K-edge densitometer as claimed in claim 14, wherein said tubular containment has a sealing section to be sealingly received in said standard adapter flange of said hot cell.

26. The hybrid K-edge densitometer as claimed in claim 14, wherein said tubular containment has a cylindrical shape in said transfer section which is considerably flattened in said measuring window section.

* * * * *